(12) United States Patent
Kurihara et al.

(10) Patent No.: US 7,242,004 B2
(45) Date of Patent: Jul. 10, 2007

(54) IMAGE CORRECTION METHOD, IMAGE CORRECTION APPARATUS, AND IMAGE CORRECTION PROGRAM

(75) Inventors: Hideyuki Kurihara, Sendai (JP); Tomohiro Kaneta, Sendai (JP)

(73) Assignee: Nihon Medi-Physics Co., Ltd. (JP)

( * ) Notice: Subject to any disclaimer, the term of this patent is extended or adjusted under 35 U.S.C. 154(b) by 38 days.

(21) Appl. No.: 11/197,208

(22) Filed: Aug. 2, 2005

(65) Prior Publication Data

US 2006/0027749 A1 Feb. 9, 2006

(30) Foreign Application Priority Data

Aug. 5, 2004 (JP) ............................ P2004-229823

(51) Int. Cl.
*A61B 6/02* (2006.01)
*G01T 1/161* (2006.01)

(52) U.S. Cl. ..................................................... 250/369

(58) Field of Classification Search ................ 250/300, 250/341.5, 369
See application file for complete search history.

(56) References Cited

U.S. PATENT DOCUMENTS

| | | | |
|---|---|---|---|
| 5,739,540 A * | 4/1998 | Motomura et al. | 250/363.04 |
| 6,175,118 B1 * | 1/2001 | Takayama et al. | 250/369 |
| 6,281,504 B1 * | 8/2001 | Takayama et al. | 250/363.07 |
| 6,950,494 B2 * | 9/2005 | Vija et al. | 378/62 |

OTHER PUBLICATIONS

Koichi Ogawa "Image distortion and correction in single photon emisssion CT", Annals of Nuclear Medicine vol. 18, No. 3, 171-185, Jan. 2004.*

Miller et al. "Planar imaging quantification using 3D attenuated correction data and Monte Carlo simulated buildup factors", Phys. Med. Biol. 41 (1196), 1401-1423, Oct. 1995.*

Guy et al. "DETECT-Dual Energy Transmission Estimation CT-for improved attenuation correction in SPECT and PET", IEEE Transactions on Nuclear Science, vol. 45, No. 3, Jun. 1998.*

Chow et al. "Attenuation correction for small animal PET", Phys. Med. Biol. 50 (2005) 1837-1850, Dec. 2004.*

Journal of Nuclear Medicine 2000, 41, 8, pp. 1364-1368.

IEEE Transactions on Medical Imaging 1994, 13, 4, pp. 601-609.

Patton et al., "Image Fusion Using an Integrated, Dual-Head Coincidence Camera with X-Ray Tube-Based Attenuation Maps." The Journal of Nuclear Medicine, vol. 41, No. 8 (Aug. 2000) pp. 1364-1368.

Hudson et al., "Accelerated Image Reconstruction Using Ordered Subsets of Projection Data." IEEE Transactions on Medical Imaging, vol. 13, No. 4 (Dec. 1994) pp. 601-609.

* cited by examiner

*Primary Examiner*—Constantine Hannaher
(74) *Attorney, Agent, or Firm*—Ostrolenk, Faber, Gerb & Soffen, LLP

(57) ABSTRACT

The image correction method according to an embodiment of the present invention includes the steps of: (a) generating an absorption correction map by replacing a CT value of each pixel of a CT image with a corresponding linear absorption coefficient and replacing the linear absorption coefficient in a bone region with the linear absorption coefficient of water or a soft biological tissue; and (b) generating a corrected image by multiplying a value of each pixel of a nuclear medical image obtained with respect to substantially the same tomographic plane as a plane in which the CT image has been obtained by a corresponding pixel of the absorption correction map.

18 Claims, 12 Drawing Sheets

Fig.12

IMAGE CORRECTION METHOD, IMAGE CORRECTION APPARATUS, AND IMAGE CORRECTION PROGRAM

BACKGROUND OF THE INVENTION

1. Field of the Invention

The present invention relates to an image correction method, an image correction apparatus, and an image correction program.

2. Related Background of the Invention

Nuclear medical images obtained by a nuclear medical inspection such as positron emission tomography (hereinafter, referred to as "PET") and single photon emission computed tomography (hereinafter, referred to as "SPECT") are widely used for diagnosing various diseases including cancer.

A nuclear medical image can be obtained by administering a medicine labeled with a radioisotope (hereinafter, referred to as a "radiopharmaceutical") to a subject and detecting the gamma rays directly or secondarily emitted from the administered medicine using a gamma camera etc. In other words, a nuclear medical image is obtained by imaging the distribution of the administered radiopharmaceutical, so that it is suited for the detection of a lesion having a specific function. For example, 2-[$^{18}$F] fluoro-2-deoxy-D-glucose, which is one of radiopharmaceuticals, has a property of being accumulated on a tumor at which sugar metabolism is raised, so that it becomes possible to specifically detect a tumor at which sugar metabolism is raised.

As described above, the nuclear medical inspection has an advantage of being capable of obtaining nuclear medical images applicable to diagnosis of various diseases by using various radiopharmaceuticals, however, there is a problem in that the image quality of a nuclear medical image is lower than that of a biological tomographic image that can be obtained by other methods such as CT imaging. For example, there is a problem of deterioration in image quality caused by the absorption of gamma rays depending on the distance from a radiation source or a problem of the lowness of contrast at a lesion.

To cope with the former problem, that is, the deterioration in image quality caused by the absorption of gamma rays, there has been proposed a method for correcting a nuclear medical image using an absorption correction map generated from a CT image and taking into account the linear absorption coefficient and the depth from the body surface (Ordered Subset Expectation Maximization method (hereinafter, referred to as an "OSEM") (for example, refer to Non-patent Document 1 and Non-patent Document 2).

[Non-patent Document 1] Patton, J. A., Delbeke, D. and Sandler, M. P., "Image Fusion Using an Integrated, Dual-Head Coincidence Camera with X-Ray Tube-Based Attenuation Maps.", The Journal of Nuclear Medicine, (USA), Society of Nuclear Medicine, 2000, 41, 8, p. 1364–1368.

[Non-Patent Document 2] Hudson, H. M. and Larkin, R. S., "Accelerated Image Reconstruction Using Ordered Subsets of Projection Data", IEEE Transactions on Medical Imaging, (USA), IEEE Engineering in Medicine and Biology Society et al., 1994, 13, 4, p. 601–609.

SUMMARY OF THE INVENTION

However, the subject for improving the contrast of a lesion in a nuclear medical image is still unresolved.

In view of the above-mentioned problems, the present invention has been made and an object thereof is to provide an image correction method, an image correction apparatus, and an image correction program capable of improving the contrast of a lesion.

An image correction method according to an aspect of the present invention comprises steps of: (a) generating an absorption correction map by replacing a CT value of each pixel of a CT image with a corresponding linear absorption coefficient and replacing the linear absorption coefficient in a bone region with a linear absorption coefficient of water or a soft biological tissue; and (b) generating a corrected image by multiplying a value of each pixel of a nuclear medical image obtained with respect to substantially the same tomographic plane as a plane in which the CT image has been obtained by a corresponding pixel value of the absorption correction map.

An image correction apparatus according to another aspect of the present invention comprises: (a) means for generating an absorption correction map by replacing a CT value of each pixel of a CT image with a corresponding linear absorption coefficient and replacing the linear absorption coefficient in a bone region with a linear absorption coefficient of water or a soft biological tissue; and (b) means for generating a corrected image by multiplying each pixel of a nuclear medical image obtained with respect to substantially the same tomographic plane as a plane in which the CT image has been obtained by a corresponding pixel of the absorption correction map.

An image correction program according to still another aspect of the present invention causes a computer to execute steps of: (a) generating an absorption correction map by replacing a CT value of each pixel of a CT image with a corresponding linear absorption coefficient and replacing the linear absorption coefficient in a bone region with a linear absorption coefficient of water or a soft biological tissue; and (b) generating a corrected image by multiplying each pixel value of a nuclear medical image obtained with respect to substantially the same tomographic plane as a plane in which the CT image has been obtained by a corresponding pixel value of the absorption correction map.

According to the present invention, an absorption correction map in which the linear absorption coefficient in a bone region, in which the linear absorption coefficient is relatively larger with respect to that in other regions, has been replaced by the linear absorption coefficient of water or a soft biological tissue is generated. Since a nuclear medical image is multiplied by the generated absorption correction map, in a resulting corrected image, background noises are reduced and the contrast of a lesion is enhanced. Further, the corrected image is generated by the replacement processing for generating an absorption correction map and the multiplication processing for generating the corrected image. Therefore, according to the present invention, the corrected image can be generated in a short time without depending on experience of an operator.

In the present invention described above, it may be possible (c1) to generate an absorption correction map by replacing the CT value of each pixel of the CT image with the corresponding linear absorption coefficient based on a predetermined correspondence between the CT value and the linear absorption coefficient, and (d1) to replace the linear absorption coefficient included in a range predetermined as the linear absorption coefficient in a bone region with the linear absorption coefficient predetermined as the linear absorption coefficient of water or the soft biological tissue.

Further, in the present invention described above, it may be possible (c2) to generate a second CT image by replacing a CT value included in a range predetermined as the CT value in a bone region among CT values of the CT image with the CT value predetermined as the CT value of water or the soft biological tissue, and (d2) to generate an absorption correction map by replacing a CT value of each pixel of the second CT image by the corresponding linear absorption coefficient based on a predetermined correspondence between the CT value and the linear absorption coefficient.

Furthermore, in the present invention, it may be possible (e) to apply to the absorption correction map a filtering processing for converting the resolution of an absorption correction map into the resolution of the nuclear medical image and (f) to generate the corrected image by multiplying the value of each pixel of the nuclear medical image by the corresponding pixel of the absorption correction map to which the filtering processing has been applied.

DESCRIPTION OF THE PREFERRED EMBODIMENTS

Preferred embodiments of the present invention are explained in detail with reference to drawings. The same symbols are attached to the same or similar parts in each drawing.

Figure 1:
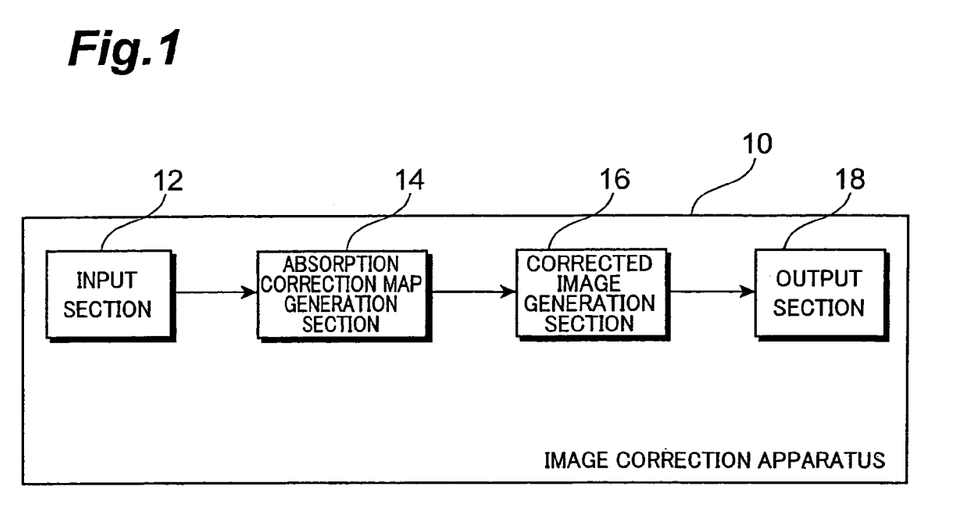
FIG. 1 is a diagram showing the configuration of an image correction apparatus according to an embodiment of the present invention.

FIG. 1 is a diagram showing the configuration of an image correction apparatus according to an embodiment of the present invention. An image correction apparatus 10 shown in FIG. 1 is, from a physical standpoint, a computer comprising a CPU (central processing unit), a hard disk, memories, a display device such as a display, input devices such as a keyboard/mouse, etc.

Figure 2:
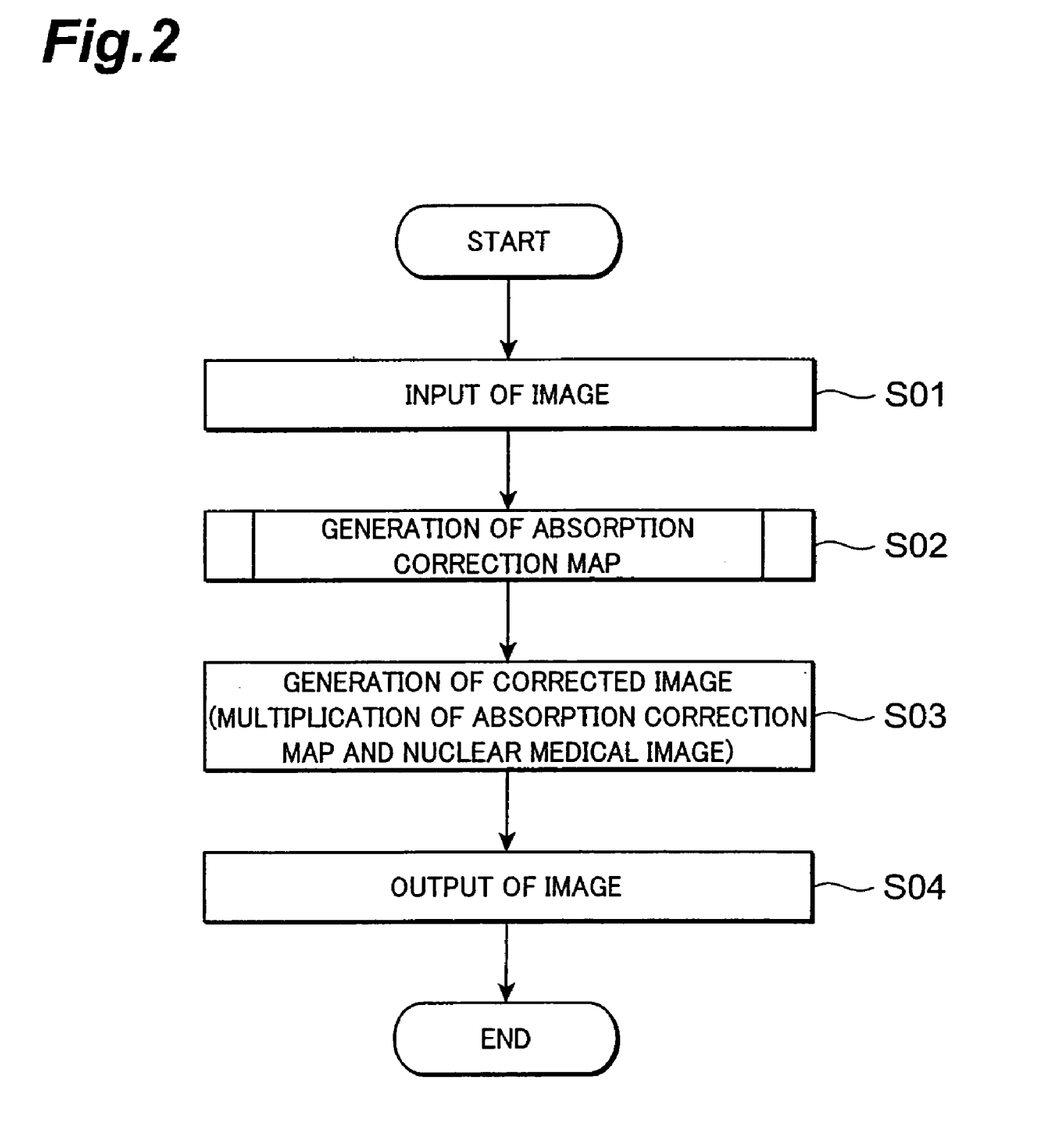
FIG. 2 is a flow chart of an image correction method according to an embodiment of the present invention.

The image correction apparatus 10 functionally comprises an input section 12, an absorption correction map generation section 14, a corrected image generation section 16, and an output section 18. The functions of these components are explained with reference to FIG. 1 and at the same time, an image correction method according to an embodiment of the present invention is explained. FIG. 2 is a flow chart of the image correction method according to the embodiment of the present invention.

The input section 12 inputs a nuclear medical image and a CT image (X-ray CT image) obtained with respect to substantially the same tomographic plane in a living body (step S01). The input section 12 inputs a nuclear medical image and a CT image obtained by, for example, a widely known SPECT-CT or PET-CT apparatus.

The SPECT-CT apparatus and the PET-CT apparatus are respectively an apparatus arrangement composed of an X-ray CT apparatus and a SPECT apparatus integrated with each other and an apparatus arrangement composed of an X-ray CT apparatus and a PET apparatus integrated with each other. It is possible for the SPECT-CT apparatus and the PET-CT apparatus to automatically acquire an X-ray CT image and a SPECT image, and an X-ray CT image and a PET image in substantially the same tomographic plane, respectively. For details of the SPECT-CT or PET-CT apparatus, refer to Keidar, Z., Israel, O. and Krausz, Y., "SPECT/CT in Tumor Imaging: Technical Aspect and Clinical Applications.", Seminars in Nuclear Medicine, (USA), Elsevier, 2003, 33, 3, p. 205–218. Hereinafter, a case where a SPECT image is used as the nuclear medical image is explained.

The absorption correction map generation section 14 generates an absorption correction map (step S02). An absorption correction map is a map in which each of the CT values of an X-ray CT image have been replaced by the corresponding linear absorption coefficient and the linear absorption coefficient in a bone region has been replaced by the linear absorption coefficient of water or a soft biological tissue. Further, in an absorption correction map, its resolution has been converted into one corresponding to the resolution of the SPECT image. The details of a method for generating an absorption correction map will be mentioned later.

The corrected image generation section 16 generates a corrected image by multiplying a value of each pixel of the nuclear medical image and the corresponding pixel value in an absorption correction map (step S03).

The output section 18 outputs the corrected image to a display device such as a display (step S04). A display on a display device by the output section 18 is performed based on the luminance or colors in accordance with the signal intensity of the corrected image. A display on a display device by the output section 18 may be not only a two-dimensional display of the corrected image but also a three-dimensional display. In the case of a three-dimensional display, plural images generated with respect to each of plural cross-sectional surfaces in a living body are format-processed (coordinate transformation processing) and a sagittal cross-sectional image and a coronary cross-sectional image are generated. By displaying these images in a two-dimensional space, a three-dimensional display can be provided.

Figure 3:
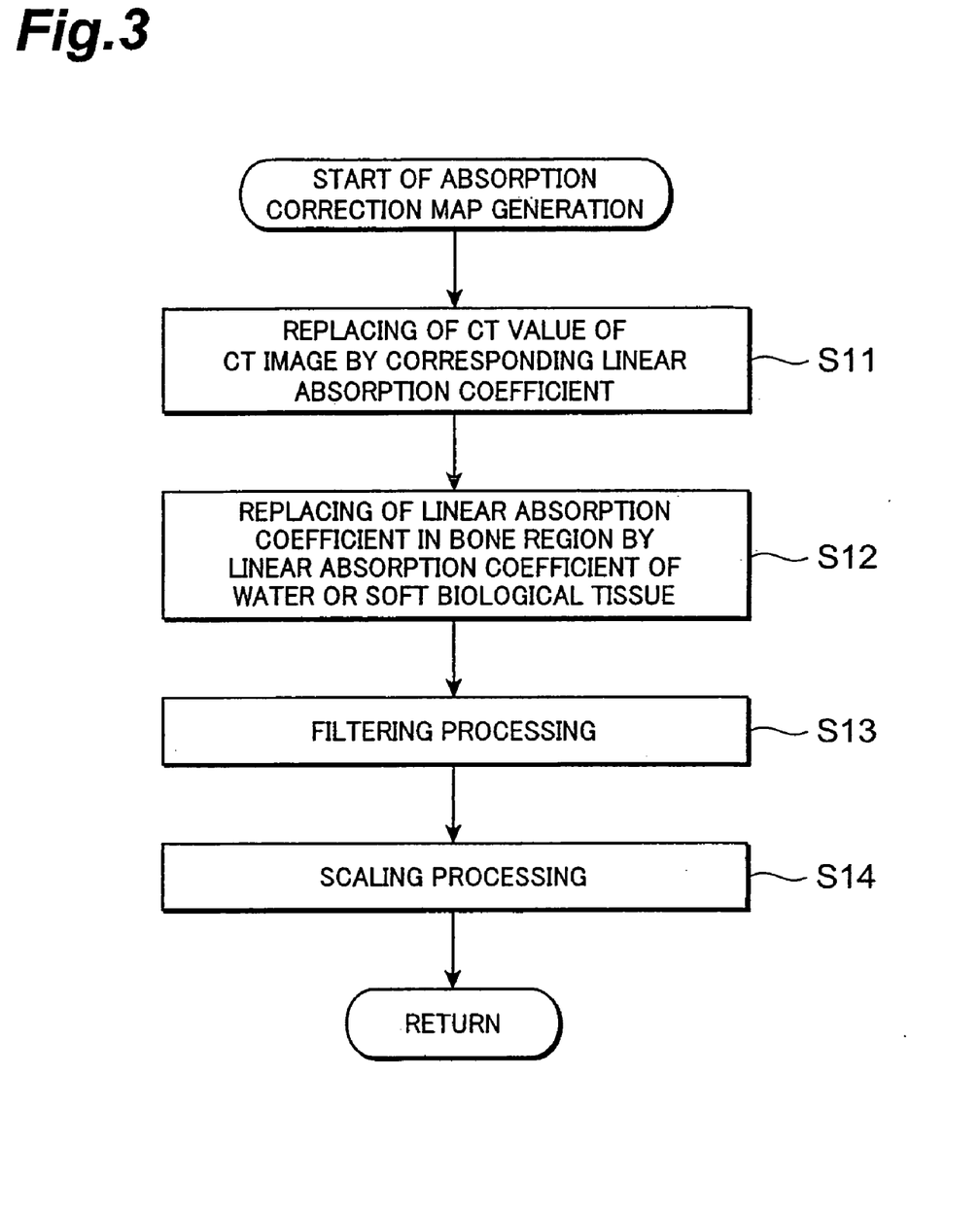
FIG. 3 is a flow chart of a processing for generating an absorption correction map.

A method for generating an absorption correction map by the absorption correction map generation section 14 is explained in detail below. FIG. 3 is a flow chart of a processing for generating an absorption correction map.

In the generation processing of an absorption correction map in the embodiment shown in FIG. 3, the absorption correction map generation section 14 first generates an absorption correction map by replacing the CT value of a CT image with the corresponding linear absorption coefficient (step S11).

The CT image is formed by a relative display in which the CT value of bone is 1,000 Hu (Hounsfield unit), the CT value of water is 0 Hu, and the CT value of air is −1,000 Hu. On the other hand, for example, at an energy level of 511 keV, the linear absorption coefficient of water (CT value=0 Hu) is 0.096/cm, the linear absorption coefficient of bone (CT=1,000 Hu) is 0.172/cm, and the linear absorption coefficient of air (CT=−1,000) is 0/cm.

The absorption correction map generation section 14 uses these values and replaces the CT values by the linear absorption coefficient using the following expression (1) for the air region (−1000≦CT value≦0) and using the following expression (2) for the water or solid region. In the following expressions (1) and (2), X is a CT value and Y is a linear absorption coefficient.

$$Y=0.000096X+0.096 \text{ (CT value<0)} \quad (1)$$

$$Y=0.000076X+0.096 \text{ (CT value>0)} \quad (2)$$

Next, the absorption correction map generation section 14 replaces the linear absorption coefficient in a bone region among the linear absorption coefficients in the absorption correction map generated in step S11 with the linear absorption coefficient of water or the soft biological tissue (step S12). For example, at an energy level of 511 keV, the linear absorption coefficient of bone is 0.172/cm. Therefore, the absorption correction map generation section 14 replaces, using a threshold value of 0.172/cm, the linear absorption coefficient exceeding the threshold value among the linear absorption coefficients in the absorption correction map generated in step S11 with 0.096/cm, which is the linear absorption coefficient of water. Thereby, the absorption correction map is generated.

Next, the absorption correction map generation section 14 carries out a filtering processing for matching the resolution of the absorption correction map with the resolution of the SPECT image (step S13). In the filtering processing, the absorption correction map generation section 14 uses the same filter as that used for reconstructing the SPECT image. As the filter, for example, a Butterworth filter is used.

In greater detail, the absorption correction map generation section 14 generates plural profiles p(s, θ) by projecting the absorption correction map. In other words, the absorption correction map generation section generates the plural profiles p(s, θ) of the absorption correction map by changing θ at a pitch of predetermined angles.

Next, the absorption correction map generation section 14 generates plural representations in frequency space $P_\theta(f)$ of the profile by the Fourier transform of each of the plural profiles p(s, θ). The absorption correction map generation section 14 generates $G_\theta(f)$ by applying the Butterworth filter B (f) shown in the following expression (3) to each of $P_\theta(f)$ as shown in the following expression (4).

$$B(f)=1/(1+(f/fc))^{2n} \quad (3)$$

$$G_\theta(f)=P_\theta(f) \cdot B(f) \quad (4)$$

In expression (3), fc is a cut-off frequency and n is an order. It is possible to use an arbitrarily selected value as the value of n, however, if n is too small, many high-frequency components are included and the statistical noises are enhanced. On the other hand, if the value of n is too large, a ring-like artifact occurs, therefore, such n is not preferable. Preferably, a value of 2 to 8 is used for n and most preferably, a value of 5 is used.

A value of fc is arbitrarily selected in accordance with the type of the used radiopharmaceutical, the region to be measured, etc., but it is required to be equal to 0.5 cycle/pixel or less. Here, if the value of fc is too large, the statistical noises are enhanced. On the other hand, if the value of fc is too small, even the necessary information is eliminated and the resolution of an image deteriorates. Therefore, if a tumor is imaged using Ga (pixel size: 0.77 cm), an fc of 0.2 to 0.3 cycle/cm is used preferably, and most preferably, an fc of 0.25 cycle/cm is used. When a tumor is imaged using FDG, a fc of 0.35 to 0.45 cycle/cm is used preferably, and most preferably, a fc of 0.4 cycle/cm is used.

Next, the absorption correction map generation section 14 obtains an absorption correction map by back projecting each of $G_\theta(f)$ in the direction of the angle θ and completes the filtering processing (step S13).

Next the absorption correction map generation section 14 applies a scaling processing to the absorption correction map (step S14). The scaling processing is a processing for preventing the signal intensity of the corrected image from exceeding the upper limit. Specifically, the absorption correction map generation section 14 obtains the numerical value N that satisfies the following expression (5) and divides each of the linear absorption coefficients of the absorption correction map by N. In the following expression (5), a is the signal intensity of each pixel of the absorption correction map, b is the signal intensity of the corresponding pixel in the image to be corrected, and Mmax is the upper limit described above. By means of the processing, the absorption correction map used for generating the corrected image is generated.

$$a \times b/N < M\text{max} \quad (5)$$

Figure 4:
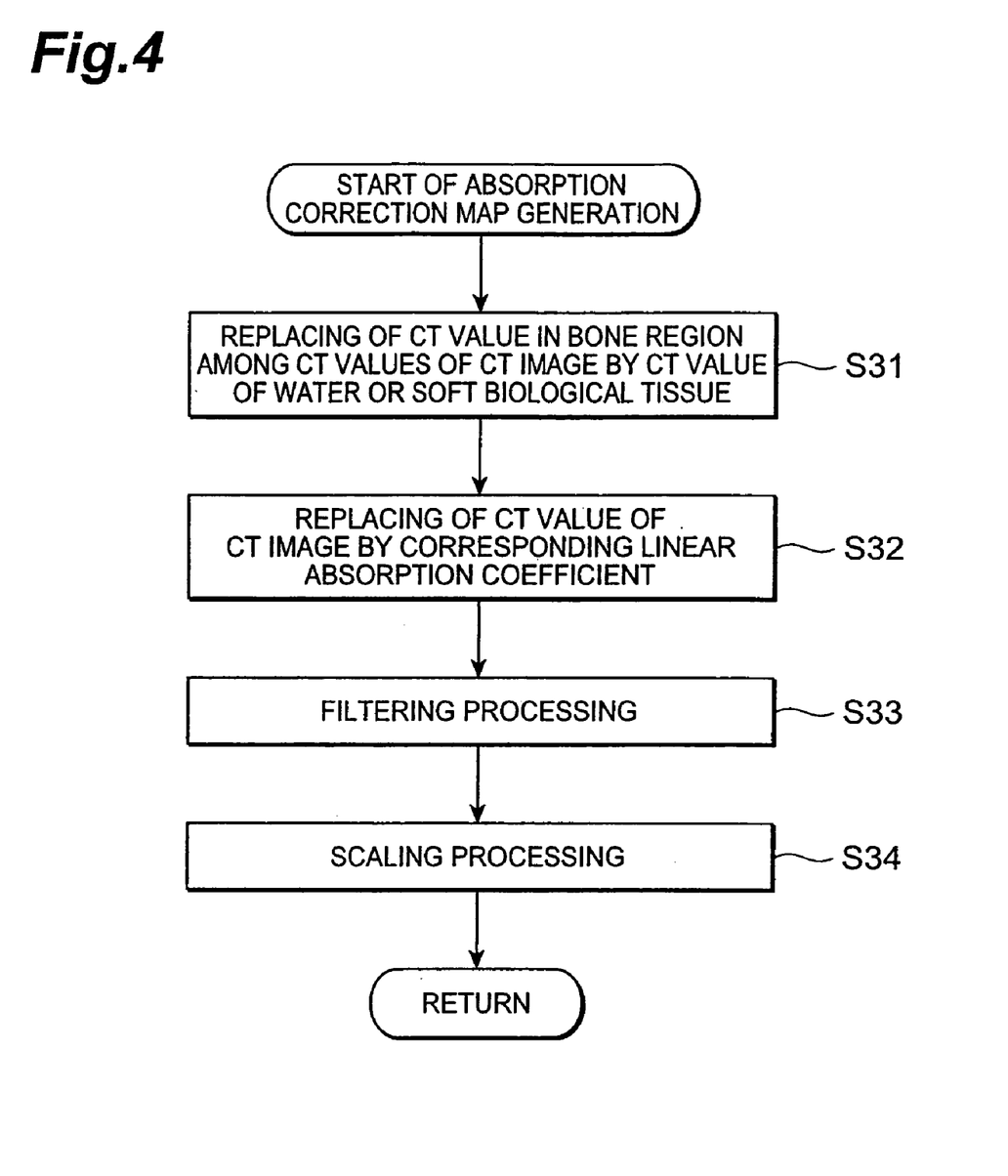
FIG. 4 is a flow chart of a processing for generating an absorption correction map in another embodiment.

A method for generating an absorption correction map in another embodiment is explained below. FIG. 4 is a flow chart showing a processing for generating an absorption correction map in another embodiment.

In a generation processing of an absorption correction map in another embodiment shown in FIG. 4, the absorption correction map generation section 14 first replaces the CT value in a bone region among the CT values of the CT image with the CT value of water or the soft biological tissue (step S31). Specifically, the absorption correction map generation section 14 replaces the CT values greater or equal to 1,000 Hu by 0 Hu.

Next, the absorption correction map generation section 14 replaces the CT values in the CT image generated by the replacement in step S31 with the corresponding linear absorption coefficient (step S32). In this replacement processing also, it is possible to use the expressions (1) and (2).

Next, the absorption correction map generation section 14 matches the resolution of the absorption correction map generated in step S32 with the resolution of the SPECT image by a processing similar to the filtering processing described above (step S33).

Next, the absorption correction map generation section 14 generates an absorption correction map used for generating a corrected image by applying the scaling processing to the absorption correction map generated in step S33 so that the relationship in the expression (5) is satisfied (step S34).

As described above, it is possible for the absorption correction map generation section 14 to generate an absorption correction map by various methods.

Figure 5:
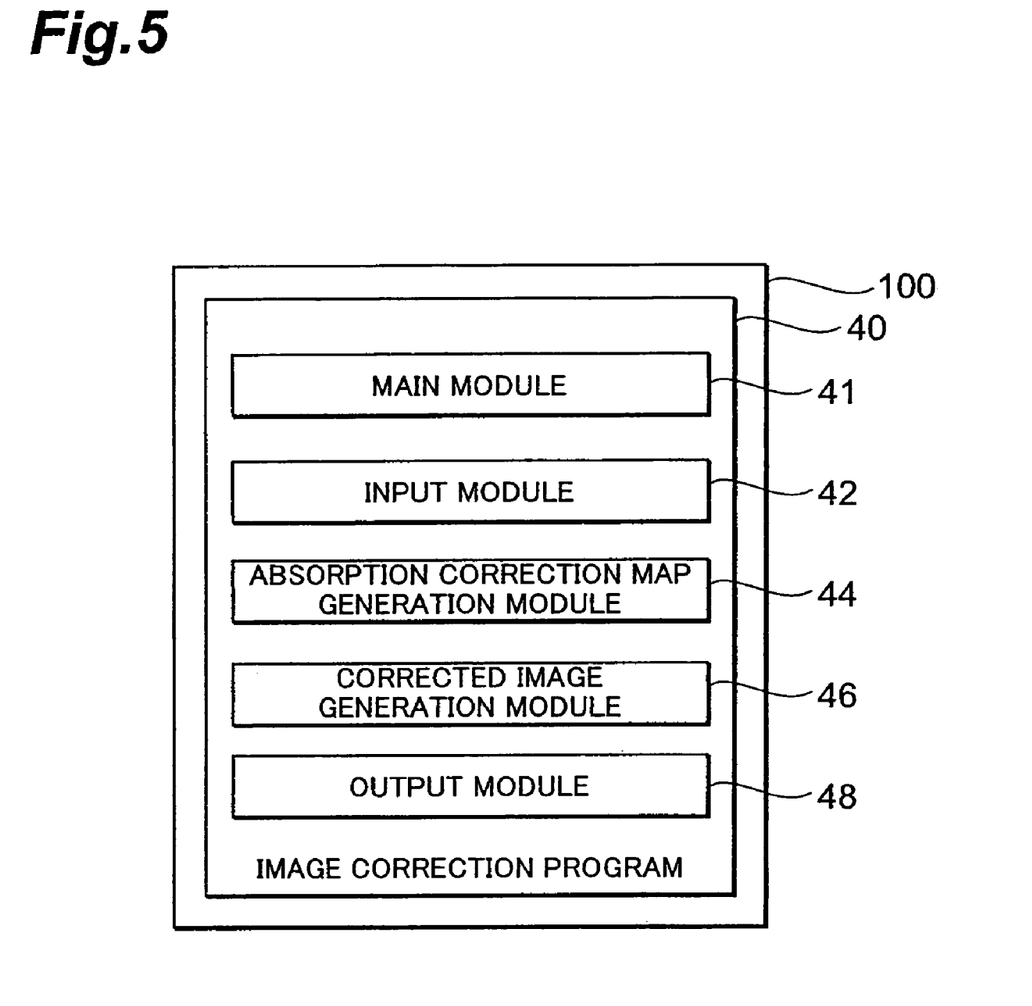
FIG. 5 is a diagram showing the configuration of an image correction program according to an embodiment of the present invention along with a recording medium.

An image correction program for causing a computer to operate as the image correction apparatus 10 is explained below. FIG. 5 is a diagram showing the configuration of an image correction program according to an embodiment of the present invention along with a recording medium.

An image correction program 40 shown in FIG. 5 is stored in a recording medium 100 so as to enable the providing of the program. As the recording medium 100, a recording medium such as flexible disk, CD-ROM, DVD, and ROM, or a semiconductor memory, etc., is shown as an example.

Figure 6:
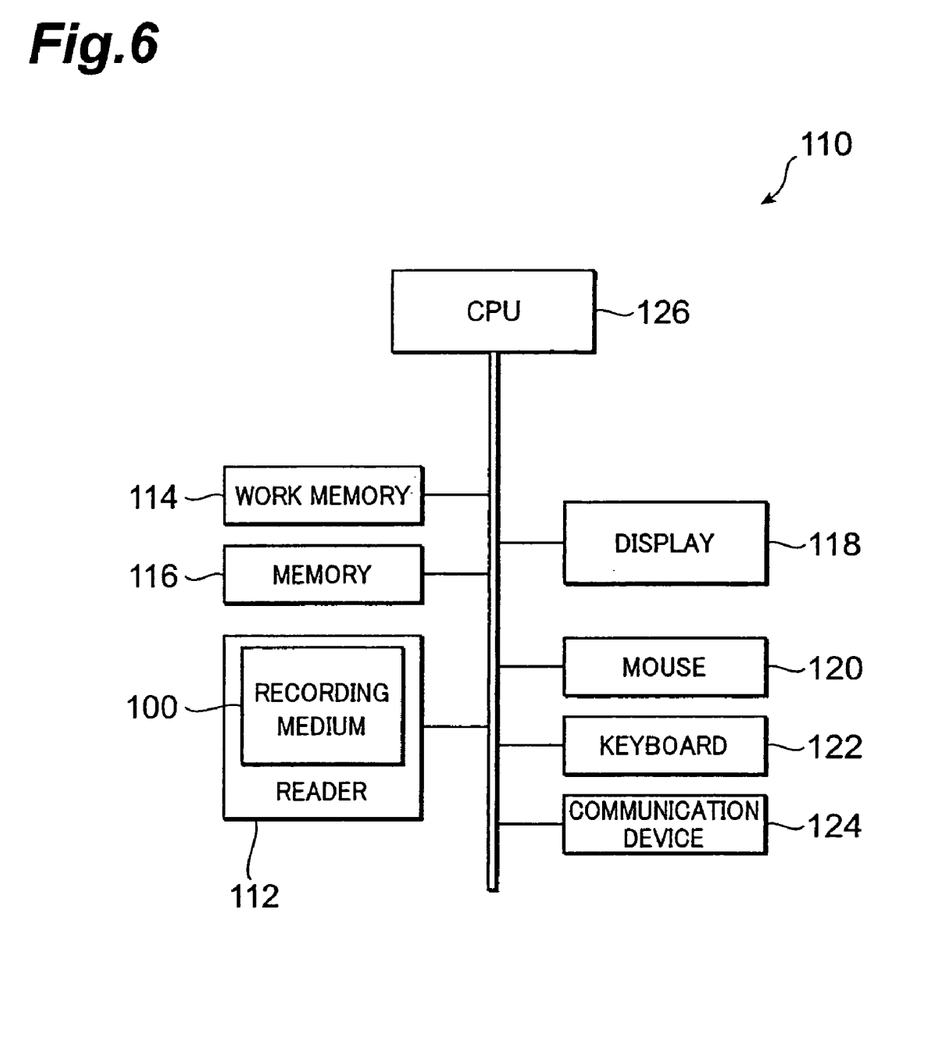
FIG. 6 is a diagram showing the hardware configuration of a computer for executing a program stored in a recording medium.
Figure 7:
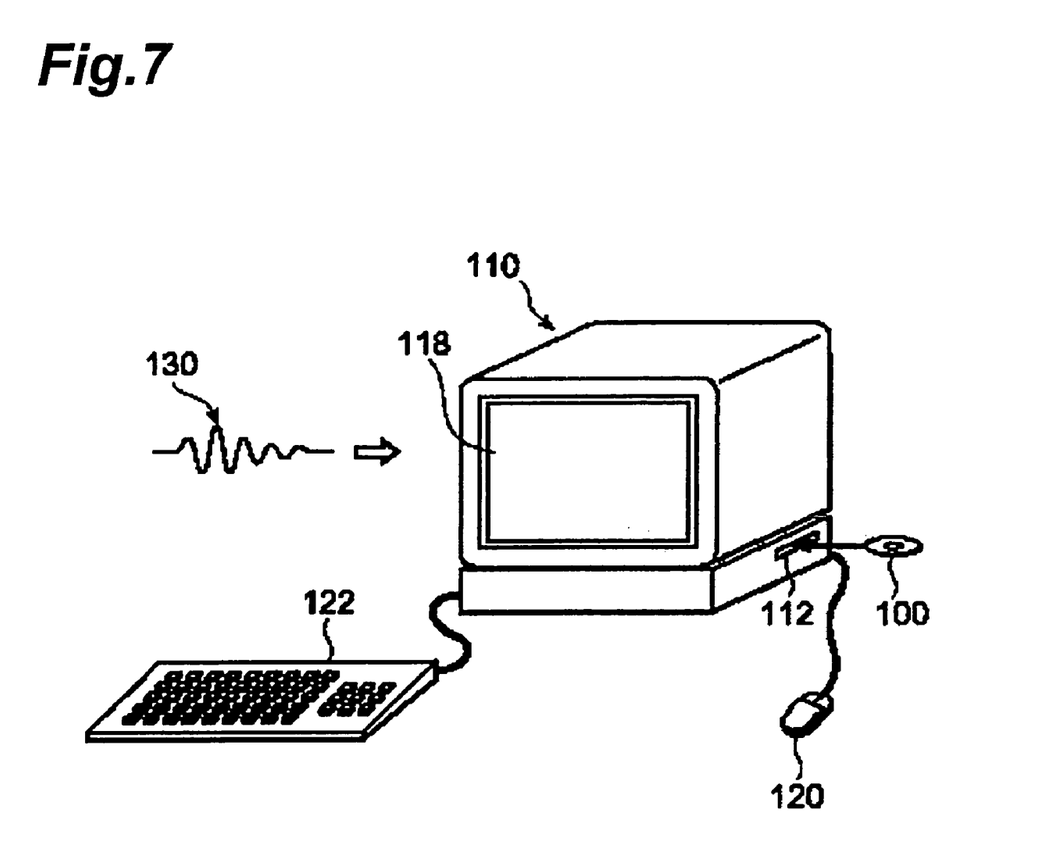
FIG. 7 is a perspective view of a computer for executing a program stored in a recording medium.

FIG. 6 is a diagram showing the hardware configuration of a computer for executing a program stored in a recording medium and FIG. 7 is a perspective view of the computer for executing the program stored in the recording medium. As shown in FIG. 6, a computer 110 comprises a reader 112 such as flexible disk drive, CD-ROM drive, and DVD drive, a work memory (RAM) 114 in which an operating system is resident, a memory 116 for storing a program stored in the recording medium 100, a display device 118 such as display, a mouse 120 and a keyboard 122, which are input devices, a communication device 124 for transmitting and receiving data, etc., and a CPU 126 for controlling the execution of a program. When the recording medium 100 is inserted into the reader 112, the computer 110 becomes capable of accessing the image correction program 40 stored in the recording medium 100 through the reader 112 and of operating as the image correction apparatus 10 by means of the image correction program 40.

As shown in FIG. 7, the image correction program 40 may be one that is provided via a network as a computer data signal 130 superimposed on carrier waves. In this case, the computer 110 may store the image correction program 40 received by the communication device 124 and execute the image correction program 40.

As shown in FIG. 5, the image correction program 40 comprises a main module 41 that controls the processing, an input module 42, an absorption correction map generation module 44, a corrected image generation module 46, and an output module 48.

The input module 42 causes a computer to execute the step S01; the absorption correction map generation module 44 causes the computer to execute the step S02; the corrected image generation module 46 causes the computer to execute the step S03; and the output module 48 causes the computer to execute the step S04.

While preferred embodiments of the present invention are explained below in greater detail, the present invention is not limited to these embodiments.

EXAMPLE 1

148 MBq of gallium 67 citrate inj. NMP for injection (a product name of Nihon Medi-Physics Co., Ltd.) was administered intravenously to a patient (aged seventy-five years, male) suffering from a malignant lymphatic tumor and a SPECT image of the thorax (transverse image) (imaging conditions: 64×64 matrix; 60 directions/360 degrees; and 30 seconds/direction) was obtained using a SPECT-CT apparatus (Millennium VG+Hawkeye, made by GEC) after 72 hours of the administration.

Next, imaging of a CT image in the same tomographic plane as that of the SPECT image was carried out (imaging conditions: 140 kV, 2.5 mA; 15 seconds/slice; and 128×128 matrix) and an absorption correction map was generated using the CT image. On the histogram of the linear absorption coefficient in the absorption correction map, the value (0.214/cm) of the linear absorption coefficient of bone was set as a threshold value and the region was classified into the bone region and the region other than the bone region. Then, the linear absorption coefficient in the bone region in the absorption correction map was replaced by the linear absorption coefficient of water (0.119/cm).

After the replacement, the filtering processing was applied to the absorption correction map and the spatial resolution of the absorption correction map was converted into the same spatial resolution as that of the SPECT image.

The signal intensity of a pixel of the absorption correction map after the filtering processing was multiplied by the signal intensity of the corresponding pixel of the SPECT image at the same position as that of the pixel of the absorption correction map, then the obtained results was shown on the screen, and thus a corrected image was obtained.

COMPARATIVE EXAMPLE 1

The SPECT image was corrected by the OSEM method by using the CT image and the SPECT image obtained in Example 1. The image processing by the OSEM method was carried out with the following parameters having been inputted using the program built in the SPECT-CT apparatus (Millennium VG+Hawkeye, made by GEC) used for imaging.

Figure 8:
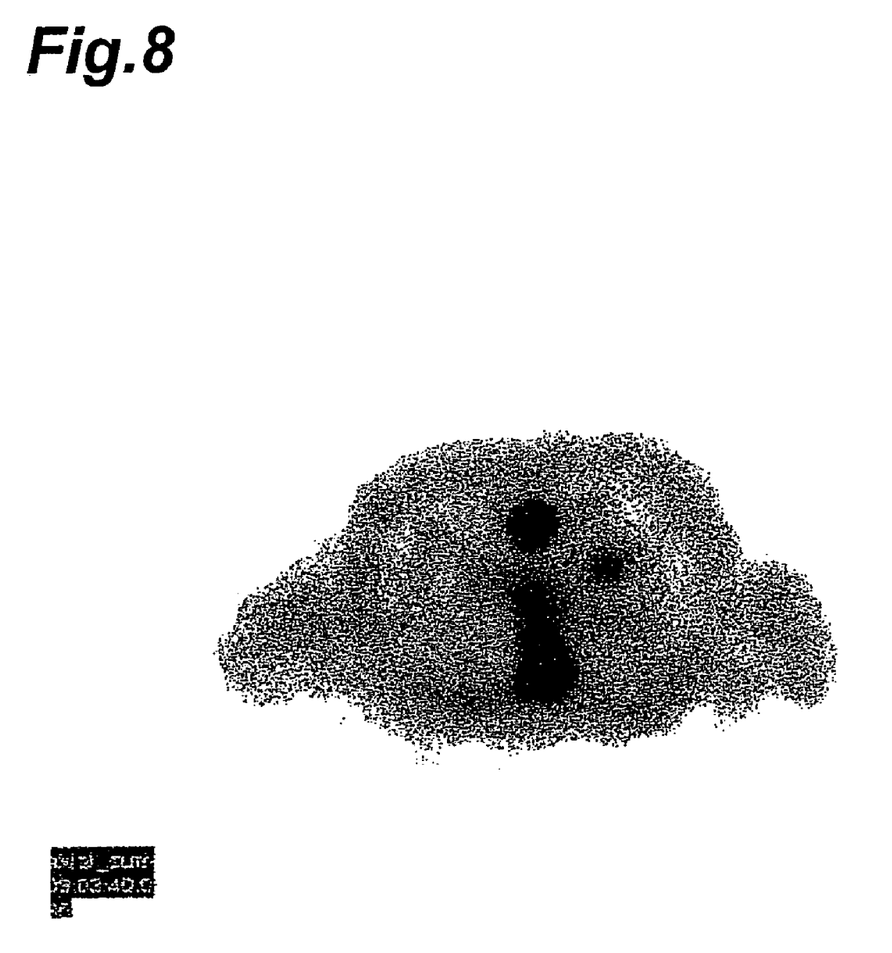
FIG. 8 is a SPECT image using example 1 and comparative example 1.
Figure 9:
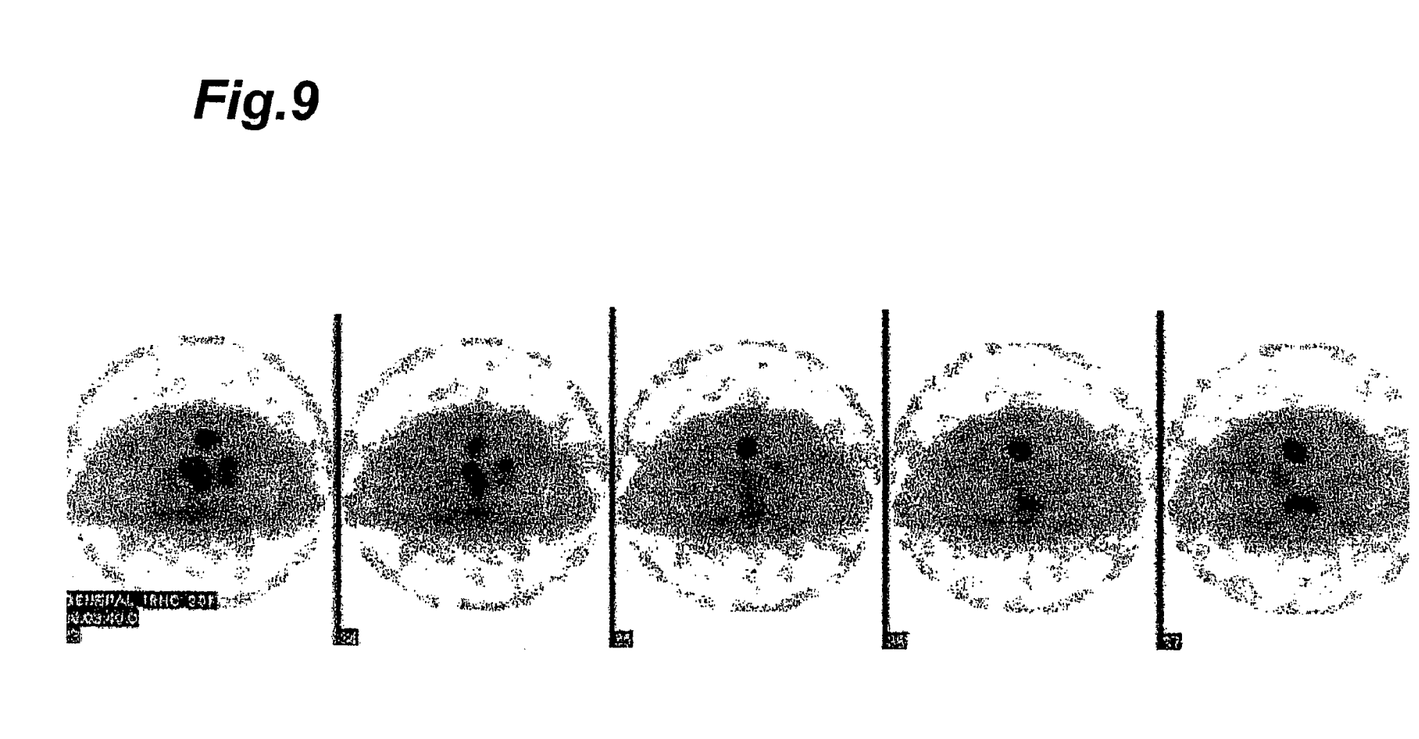
FIG. 9 is a SPECT image using example 1 and comparative example 1.
Figure 10:
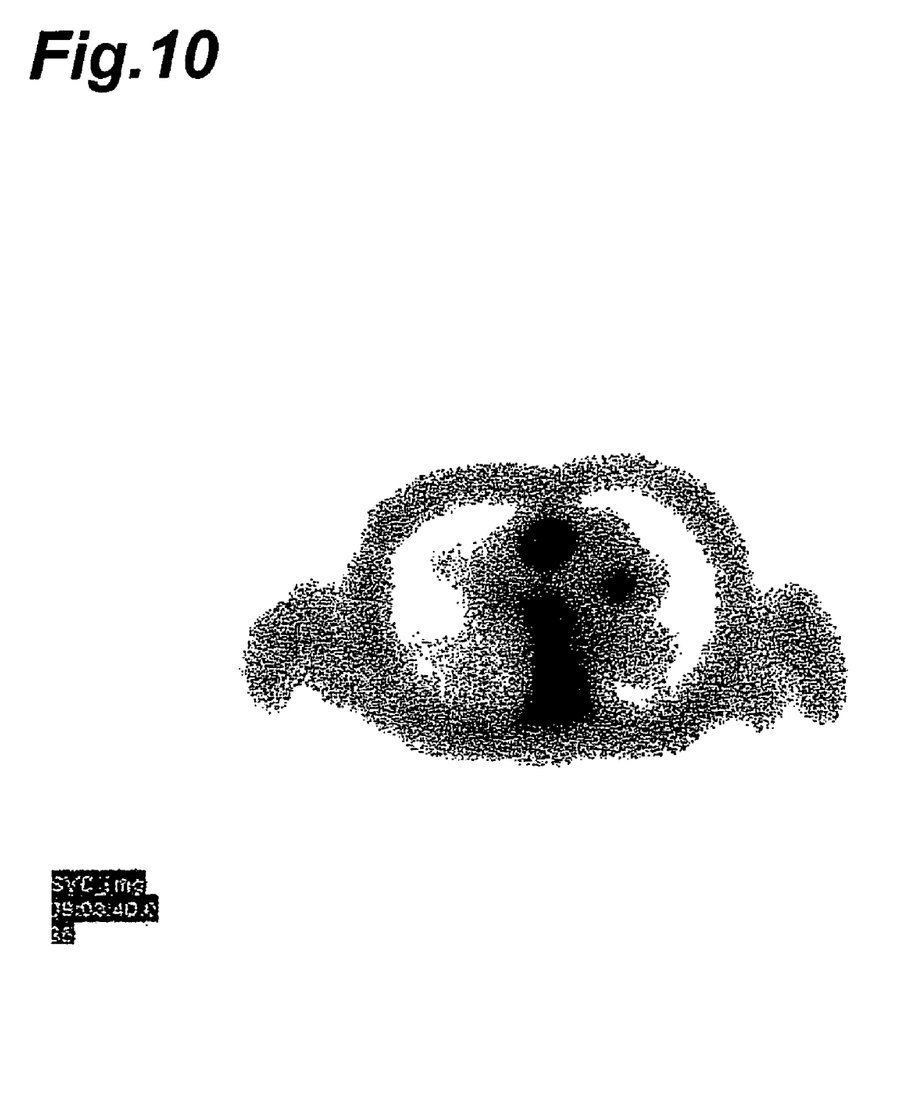
FIG. 10 is a corrected image in example 1 of the SPECT image in FIG. 8.
Figure 11:
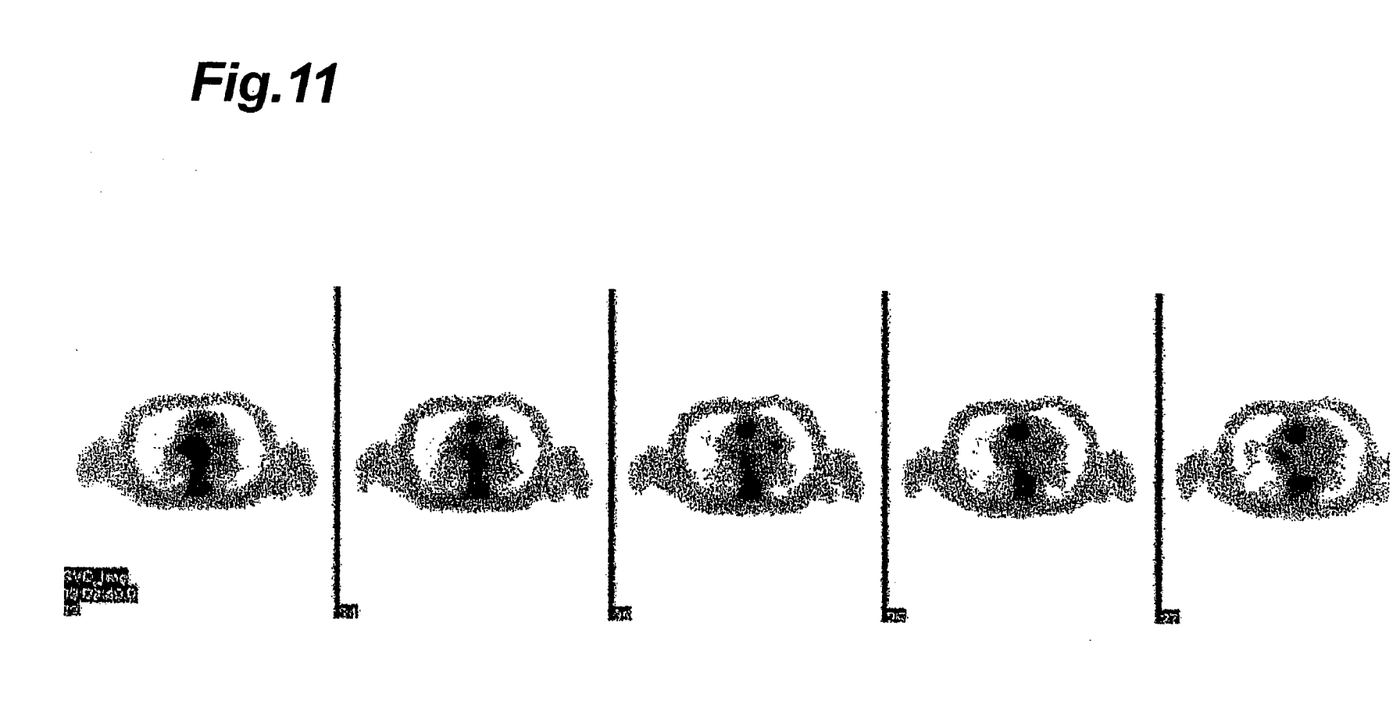
FIG. 11 is a corrected image in example 1 of the SPECT image in FIG. 9.
Figure 12:
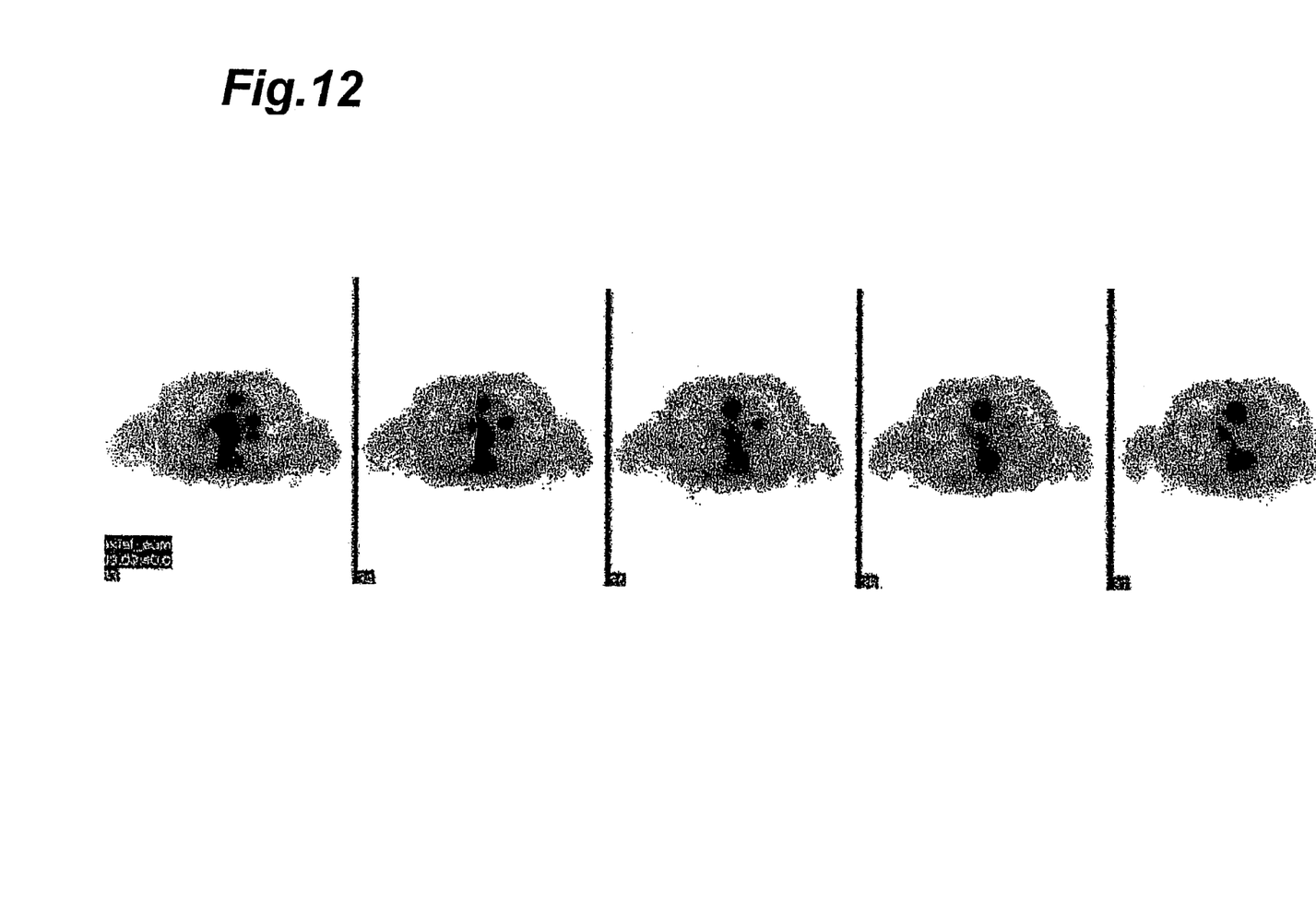
FIG. 12 is a corrected image in comparative example 1 of the SPECT image in FIG. 9.

Number of subsets: 10
Number of repeated calculations: 4
Filter used: three-dimensional Butterworth filter FIG. 8 and FIG. 9 are the SPECT images used in Example 1 and Comparative example 1 and FIG. 9 shows a series of each SPECT image of the plural cross-sections. FIG. 10 is the corrected image in Example 1 of the SPECT image in FIG. 8, FIG. 11 is the corrected image in Example 1 of the SPECT image in FIG. 9, and FIG. 12 is the corrected image in Comparative example 1 of the SPECT image in FIG. 9.

As is apparent from the reference to FIG. 8 to FIG. 12, in Example 1, there has been achieved a corrected image in which the background noises are reduced and the contrast of the lesion is improved as compared with Comparative example 1, with a sharp contour of the lesion.

Preferred embodiments of the present invention have been described above. As demonstrated in the descriptions of these embodiments, the present invention provides an image correction method, an image correction apparatus, and an image correction program capable of obtaining a corrected image that is a nuclear medical image obtained by PET and SPECT in which the contrast of a lesion has been improved, and also capable of obtaining the corrected image in a short time without relying on the experience of an expert in the related technology.

What is claimed is:

1. An image correction method comprising the steps of:
generating an absorption correction map by replacing a CT value of each pixel of a CT image with a corresponding linear absorption coefficient and replacing the linear absorption coefficient in a bone region with a linear absorption coefficient of water or a soft biological tissue; and
generating a corrected image by multiplying a value of each pixel of a nuclear medical image obtained with respect to substantially the same tomographic plane as a plane in which the CT image has been obtained by a corresponding pixel value of the absorption correction map.

2. The image correction method according to claim 1, wherein, in the step of generating the absorption correction map, the absorption correction map is generated by replacing the CT value in each pixel of the CT image with the corresponding linear absorption coefficient based on a predetermined correspondence between the CT value and the linear absorption coefficient, and replacing the linear absorption coefficient included in a range predetermined as the linear absorption coefficient in a bone region among linear absorption coefficients in the absorption correction map with the linear absorption coefficient predetermined as the linear absorption coefficient of water or the soft biological tissue.

3. The image correction method according to claim 2, wherein:
   in the step of generating the absorption correction map, a filtering processing for converting resolution of the absorption correction map into resolution of the nuclear medical image is applied to the absorption correction map; and
   in the step of generating the corrected image, the corrected image is generated by multiplying the value of each pixel of the nuclear medical image by the corresponding pixel value of the absorption correction map to which the filtering processing has been applied.

4. The image correction method according to claim 1, wherein, in the step of generating the absorption correction map, a second CT image is generated by replacing a CT value included in a range predetermined as the CT value in a bone region among CT values of the CT image by a CT value predetermined as the CT value of water or the soft biological tissue, and the absorption correction map is generated by replacing a CT value of each pixel of the second CT image with the corresponding linear absorption coefficient based on a predetermined correspondence between the CT value and the linear absorption coefficient.

5. The image correction method according to claim 4, wherein:
   in the step of generating the absorption correction map, a filtering processing for converting resolution of the absorption correction map into resolution of the nuclear medical image is applied to the absorption correction map; and
   in the step of generating the corrected image, the corrected image is generated by multiplying the value of each pixel of the nuclear medical image by the corresponding pixel value of the absorption correction map to which the filtering processing has been applied.

6. The image correction method according to claim 1, wherein:
   in the step of generating the absorption correction map, a filtering processing for converting resolution of the absorption correction map into resolution of the nuclear medical image is applied to the absorption correction map; and
   in the step of generating the corrected image, the corrected image is generated by multiplying the value of each pixel of the nuclear medical image by the corresponding pixel value of the absorption correction map to which the filtering processing has been applied.

7. An image correction apparatus comprising:
   means for generating an absorption correction map by replacing a CT value of each pixel of a CT image with a corresponding linear absorption coefficient and replacing the linear absorption coefficient in a bone region with a linear absorption coefficient of water or a soft biological tissue; and
   means for generating a corrected image by multiplying a value of each pixel of a nuclear medical image obtained with respect to substantially the same tomographic plane as a plane in which the CT image has been obtained by a corresponding pixel value of the absorption correction map.

8. The image correction apparatus according to claim 7, wherein the means for generating an absorption correction map generates an absorption correction map by replacing the CT value of each pixel of the CT image with the corresponding linear absorption coefficient based on a predetermined correspondence between the CT value and the linear absorption coefficient, and replacing the linear absorption coefficient included in a range predetermined as the linear absorption coefficient in a bone region among linear absorption coefficients in the absorption correction map with the linear absorption coefficient predetermined as the linear absorption coefficient of water or a soft biological tissue.

9. The image correction apparatus according to claim 8, wherein:
   the means for generating the absorption correction map applies a filtering processing for converting resolution of the absorption correction map into resolution of the nuclear medical image to the absorption correction map; and
   the means for generating the corrected image generates the corrected image by multiplying the value of each pixel of the nuclear medical image by the corresponding pixel value of the absorption correction map to which the filtering processing has been applied.

10. The image correction apparatus according to claim 7, wherein the means for generating the absorption correction map generates the absorption correction map by generating a second CT image by replacing a CT value included in a range predetermined as the CT value in a bone region among CT values in the CT image by the CT value predetermined as the CT value of water or the soft biological tissue and replacing a CT value of each pixel of the second CT image with the corresponding linear absorption coefficient based on a predetermined correspondence between the CT value and the linear absorption coefficient.

11. The image correction apparatus according to claim 10, wherein:
   the means for generating the absorption correction map applies a filtering processing for converting resolution of the absorption correction map into resolution of the nuclear medical image to the absorption correction map; and
   the means for generating the corrected image generates the corrected image by multiplying the value of each pixel of the nuclear medical image by the corresponding pixel value of the absorption correction map to which the filtering processing has been applied.

12. The image correction apparatus according to claim 7, wherein:
   the means for generating the absorption correction map applies a filtering processing for converting resolution of the absorption correction map into resolution of the nuclear medical image to the absorption correction map; and
   the means for generating the corrected image generates the corrected image by multiplying the value of each pixel of the nuclear medical image by the corresponding pixel value of the absorption correction map to which the filtering processing has been applied.

13. An image correction program stored on a computer-readable medium for causing a computer to execute steps of:
   generating an absorption correction map by replacing a CT value of each pixel of a CT image with a corresponding linear absorption coefficient and replacing the linear absorption coefficient in a bone region with a linear absorption coefficient of water or a soft biological tissue; and
   generating a corrected image by multiplying a value of each pixel value of a nuclear medical image obtained with respect to substantially the same tomographic plane as a plane in which the CT image has been obtained by a corresponding pixel value of the absorption correction map.

14. The image correction program according to claim 13, wherein in the step of generating the absorption correction map, the program causes a computer to execute the steps of:
generating the absorption correction map by replacing the CT value in each pixel of the CT image with the corresponding linear absorption coefficient based on a predetermined correspondence between the CT value and the linear absorption coefficient; and
replacing the linear absorption coefficient included in a range predetermined as the linear absorption coefficient in a bone region among the linear absorption coefficients in the absorption correction map with the linear absorption coefficient predetermined as the linear absorption coefficient of water or a soft biological tissue.

15. The image correction program according to claim 14, wherein the program further causes a computer to execute the steps of:
applying a filtering processing for converting resolution of the absorption correction map into resolution of the nuclear medical image to the absorption correction map in the step of generating the absorption correction map; and
generating the corrected image by multiplying a value of each pixel of the nuclear medical image by the corresponding pixel value of the absorption correction map to which the filtering processing has been applied in the step of generating the corrected image.

16. The image correction program according to claim 13, wherein in the step of generating the absorption correction map, the program causes a computer to execute the steps of:
generating a second CT image by replacing a CT value included in a range predetermined as the CT value in a bone region among CT values in the CT image with the CT value predetermined as the CT value of water or the soft biological tissue; and
generating the absorption correction map by replacing a CT value of each pixel in the second CT image with the corresponding linear absorption coefficient based on a predetermined correspondence between the CT value and the linear absorption coefficient.

17. The image correction program according to claim 16, wherein the program further causes a computer to execute the steps of:
applying a filtering processing for converting resolution of the absorption correction map into resolution of the nuclear medical image to the absorption correction map in the step of generating the absorption correction map; and
generating the corrected image by multiplying a value of each pixel of the nuclear medical image by the corresponding pixel value of the absorption correction map to which the filtering processing has been applied in the step of generating the corrected image.

18. The image correction program according to claim 13, wherein the program further causes a computer to execute the steps of:
applying a filtering processing for converting resolution of the absorption correction map into resolution of the nuclear medical image to the absorption correction map in the step of generating the absorption correction map; and
generating the corrected image by multiplying a value of each pixel of the nuclear medical image by the corresponding pixel value of the absorption correction map to which the filtering processing has been applied in the step of generating the corrected image.

* * * * *